United States Patent [19]

Sepponen

[11] Patent Number: 4,543,959
[45] Date of Patent: Oct. 1, 1985

[54] DIAGNOSIS APPARATUS AND THE DETERMINATION OF TISSUE STRUCTURE AND QUALITY

[75] Inventor: Raimo Sepponen, Helsinki, Finland

[73] Assignee: Instrumentarium Oy, Finland

[21] Appl. No.: 695,403

[22] Filed: Jan. 25, 1985

Related U.S. Application Data

[63] Continuation of Ser. No. 382,153, May 26, 1982, abandoned.

[30] Foreign Application Priority Data

Jun. 4, 1981 [FI] Finland ............................ 811733

[51] Int. Cl.$^4$ ............................................. A61B 5/04
[52] U.S. Cl. ................................... 128/653; 128/660; 324/309
[58] Field of Search ............... 128/653, 660; 324/309

[56] References Cited

U.S. PATENT DOCUMENTS

| | | | |
|---|---|---|---|
| 3,448,606 | 6/1969 | Flaherty | 73/67.8 |
| 3,789,832 | 2/1974 | Damadian | 128/653 |
| 3,932,805 | 1/1976 | Abe | 324/309 |
| 4,015,196 | 3/1977 | Moore | 324/309 |
| 4,021,726 | 5/1977 | Garroway | 324/309 |
| 4,070,611 | 1/1978 | Ernst | 324/309 |
| 4,240,439 | 12/1980 | Abe | 128/653 |
| 4,291,578 | 9/1981 | Hetz | 128/660 |
| 4,361,807 | 11/1982 | Burl | 324/309 |
| 4,385,634 | 5/1983 | Bowen | 128/660 |

OTHER PUBLICATIONS

Wells, P. N. T., "UTS in Clinical Diagnosis" Churchill Livingstone, N.Y. 1977, p. 3.
Witcovski et al. editors, "NMR Imaging" Proc. of Int. Symposium of NMR, Bowman Gray School of Medicine, Winston-Salem, N.C., Oct. 1-3, 1981, pp. 29-30, 70.

Primary Examiner—Kyle L. Howell
Assistant Examiner—Francis J. Jaworski
Attorney, Agent, or Firm—Andrus, Sceales, Starke & Sawall

[57] ABSTRACT

The invention relates to a diagnosis apparatus for simultaneously collecting information on tissue structure and tissue quality from a target, e.g. human body to be examined. The apparatus of the invention comprises means (1) for emitting ultrasonic pulses and for detecting and registering reflections from the interfaces between tissues in target area (16) determined by said means, and means (10) for processing the information obtained from a target area by means of said ultrasonic pulses as well as means (8) for visualizing the information for finding and localizing tissue area to be characterized.

The apparatus is further provided with elements (2, 3, 11, 12, 13) for collecting tissue identification information by means of a nuclear magnetic resonance or NMR-phenomenon from target to be examined in manner that the tissue identification area (19) sensitive to nuclear magnetic resonanse is arranged to be produced in said target area (16) localized and visualized by ultrasonic pulses for immediate analysis on said tissue area to be characterized.

11 Claims, 3 Drawing Figures

DIAGNOSIS APPARATUS AND THE DETERMINATION OF TISSUE STRUCTURE AND QUALITY

BACKGROUND OF THE INVENTION

This application is a continuation of application Ser. No. 06/382,153, filed May 26, 1982 now abandoned.

Ultrasound is applied in medical diagnostics for the examination of several various malady conditions and also for the observation of the development of various normal considered conditions (such as pregnancy) or for the examination of anatomical structures.

In modern ultrasonic assemblies, an image is created of tissues below an examination sensor by employing various electrical or mechanical solutions for effecting the scanning motion of an ultrasonic beam or for the creation of a planar front of ultrasonic waves. The image is created by emitting an ultrasonic pulse by means of a matrix sensor made e.g. of a piezoelectric material (in other words, a sensor consisting of a line of sensor elements of piezoelectric material), said pulse propagating as a planar wave in sub-sensor tissues. When meeting a surface where acoustic impedance, i.e. the propagating velocity of ultrasound, rapidly changes, a part of the wave front proportional to the intensity of said change is reflected back to the crystal matrix which, immediately after emitting a pulse, seeks to detect returning echoes.

A processing unit mounted on the crystal matrix defines the position of a reflection surface relative to the longitudinal direction of said matrix and, on the basis of a time interval between the pulse emitting moment and the echo returning moment, the distance of a reflection surface from the crystal matrix. Thus, the operation is analogous to that of a radar. Said processing unit now produces a plan view of the reflection surfaces below a crystal matrix. Since acoustic impedance usually changes while the ultrasonic front propagates through tissue interfaces, the image received complies relatively well with the tissue structure of an organism.

A well-known weakness of ultrasonic diagnostics is its poor tissue characterizing ability. For example, water, blood, a dense-fiber muscular tissue and spleen tissue look like similar echoless areas in an ultrasonic image. The same way, e.g. reflections producing intra-liver tissue variations may be caused by malignant tissue growth, connective tissue growth or gangrene but further examinations are required to discover their nature. This lack of tissue characterizing ability limits the use of ultrasound in diagnostics and considerably complicates the interpretation of ultrasonic results.

A new and developing imaging method is so-called NMR-imaging, nuclear spin resonance, the basic idea of which was introduced by Prof. Lauterbur in 1973. (NMR=Nuclear Magnetic Resonance.)

In NMR-imaging, superposed over a target area is a relatively intensive, very homogeneous magnetic field Bo. The nuclei of certain elements, e.g. those of hydrogen, phosphor, fluorine etc. have a magnetic moment. Majority of the nuclei with a magnetic moment in the target settle in the direction of an external magnetic field, in other words, in the minimum energy state. Subjected to the study is normally a large number of nuclei and, thus, the vector sum of magnetic moments of the nuclei, a so-called net magnetization.

For example, if a target containing e.g. hydrogen atoms is positioned in said field Bo, the net magnetization of hydrogen atoms will settle in the direction of Bo, in a so-called state of minimum energy. By applying electromagnetic energy to said group of hydrogen atoms it is possible to deflect the direction of said net magnetization from that of Bo. By the action of Bo, the deflected net magnetization is now forced to effect so-called precession motion around the direction of Bo. The angular frequency Wo of this precession motion is determined by the physical laws, so that it is directly proportional to the intensity of a field Bo over the group of nuclei. Wo is a so-called Larmor speed which depends on a so-called gyromagnetic ratio of the precessing nuclei, and each different element nucleus with a magnetic moment has its inherent Larmor speed.

$$Wo = G \cdot Bo, \text{ wherein } G = \text{gyromagnetic ratio} \quad (1)$$

A bundle of nuclei charged with electromagnetic energy gradually gives up the obtained energy and net magnetization returns to the direction of an external magnetic field. This return process is exponential in nature and characterized by a time constant $T_1$.

It should be noted that the bundle of nuclei is capable of receiving energy at frequency $f_{res}$ which is directly proportional to Larmor speed. Fres is Lamour frequency.

$$f_{res} = WO/2\pi \quad (2)$$

$f_{res}$ is generally on the radio frequency range, e.g. for hydrogen, when Bo=0.1 TESLA, $f_{res}$ is approximately 4.25 MHz.

The precessing magnetization generates a variable magnetic field detectable by means of a single coil through which the variable field passes. The electromagnetic force induced in said coil is directly proportional to the intensity of net magnetization or the number of nuclei in a target. The frequency of the in the coil induced electromagnetic force is fres in the coil induced. Since different nuclei in said bundle of nuclei lie in magnetic fields different from each other as a result of e.g. the inhomogeneity of an external magnetic field Bo and the interactions of a magnetic field produced by the nuclei around themselves, a signal inducing in the coil attenuates exponentially with time constant $T_2$. Thus, the precessing nuclei loose their face coherence since the angular frequencies of said nuclei differ slightly from each other. Thus, $T_2$ characterizes material properties if Bo is very homogeneous.

In NMR-imaging, use is made of the dependency of a Larmor frequency of the nuclei as well as the dependency of a frequency of the coil induced electromagnetic force upon the intensity of an external magnetic field acting on the precessing nuclei. By exciting the nuclei of a target with a pulse of radio frequency and by observing the precession of nuclei in a magnetic field of locally varying intensity, it is in principle possible to survey the distribution of nuclei and hence effect the NMR-imaging.

There are several NMR-imaging methods which differ from each other in detail. Those have been described e.g. in the following publications, Lauterbur: Nature Vol 242 Mar. 16, 1973 p. 190–191, Garroway et al: U.S. Pat. No. 4,021,726, Ernst: U.S. Pat. No. 4,070,611, Moore et al: U.S. Pat. No. 4,015,196. There are also several published ways of collecting NMR-information from within a target to be examined from a certain area. In this case, the localization is effected e.g.

by arranging a magnetic field superposed over a target so that the resonance condition is met in a certain spot only, or so that the homogeneity of said field is good in a certain area only and, outside this area, the inhomogeneity of the field results in the rapid weakening of a signal. Solutions of the above type have been described in publications: Damadian: U.S. Pat. No. 3,789,832, ABE: U.S. Pat. No. 3,932,805 and ABE et al: U.S. Pat. No. 4,240,439.

All the above procedures serve to collect information on the distribution of so-called free water as well as on the nature and amount of impurities contained in this water. For example, a relaxation time $T_1$ changes along with a change in the viscosity of an aqueous solution: as viscosity increases, relaxation time $T_1$ grows shorter. Hence, for example, water and blood can be distinguished from each other: $T_1$ of pure water is circa 3 sec and that of blood circa 0.6 sec. In a malignant tumor tissue, the bonding of water to proteins becomes weaker and the amount of intercellular liquid increases, these factors leading to a longer relaxation time $T_1$ relative to relaxation time $T_1$ of a normal tissue.

Generally speaking, the amount of free water as well as relaxation times of various organs differ from each other, so tissue characterizing can be quite well effected by means of NMR.

On the present level of technology the production of NMR-images is relatively slow: collection of the information required for an abdominal cross-sectional view takes approximately 60 sec. Thus, the obtainable resolution is circa $3 \times 3$ mm$^2$ and the slice thickness is circa 1 cm. Due to the movement of organs, such slow imaging process leads to deterioration of the information received and impairs the characterization of tissues. In addition, the field gradients required by the imaging process hamper the discovery of $T_2$-information without special arrangements which again require more imaging time.

Moreover, in NMR-imaging it is necessary to select a plane of imaging, i.e. an area for the NMR-survey. One example of doing this is to place a field gradient in a selected direction of a target, for example a human body. An exciting RF-pulse is provided with a narrow frequency band, so it excites a narrow slice of a target.

In a NMR-imaging assembly, a patient must be positioned in a space surrounded by a transmitter and receiver as well as sets of coils for producing the field gradients. This will complicate the treatment and observation of a patient e.g. in the case of potential cardiac complications. In addition, many patients may experience phobia or fear which add to the movement of a patient's body and affect the quality of the information obtained.

SUMMARY OF THE INVENTION

An object of the invention is to provide an apparatus whereby the preferred characteristics of ultrasonic images and NMR-imaging can be combined in a manner so far unknown for obtaining reliable and sufficient tissue information from within a target to be examined, for example a human body. Another object of the invention is to provide an apparatus which is constructionally and functionally simple, reliable and easy to operate.

Objects of the invention are accomplished in a manner set forth in detail in the accompanying claim 1 and subclaims. The arrangement according to the invention provides a novel apparatus for medical diagnostics capable with previously unattainable accuracy of characterizing tissues of a body completely non-invasively, i.e. without penetrating into the tissues. An essential characteristic of the apparatus is that an area to be surveyed is localized by means of ultrasonic beaming, said area being analyzed immediately by means of NMR-survey.

DESCRIPTION OF THE DRAWINGS

In the following the invention is described in more detail with reference to the accompanying drawing in which.

DESCRIPTION OF THE ILLUSTRATED EMBODIMENT

Figure 1:
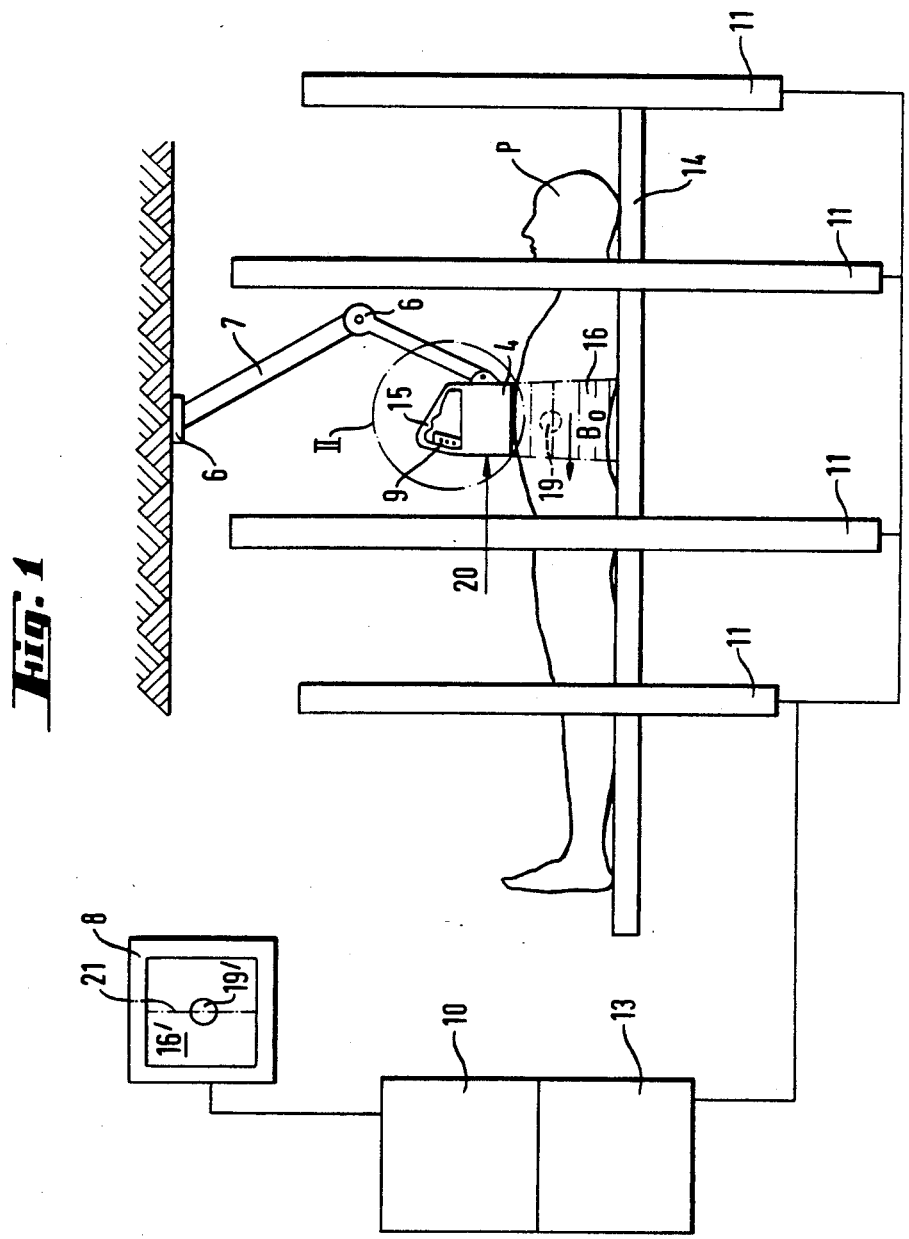
FIG. 1 shows the principle of one embodiment of a diagnosis apparatus according to the invention.
Figure 2:
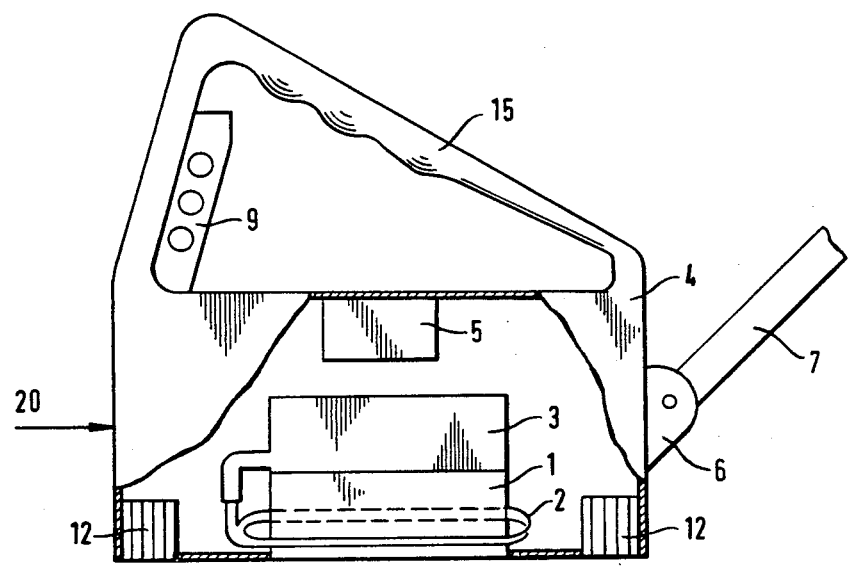
FIG. 2 shows spot II of FIG. 1 to a larger scale.

Referring to FIGS. 1 and 2, an apparatus of the invention comprises an ultrasonic matrix sensor 1, a coil assembly 2 working as an NMR-transmitter/receiver, an NMR-preamplifier 3, a protective casing 4 for the entire sensor unit 20, an NMR-locking assembly 5, a sensor arm 7, resolvers or angular sensors 6 for obtaining place and positional information, a display means 8, a control panel 9 for controlling the information collection, an ultrasonic and NMR-information processing unit 10, an electromagnet 11 for producing a homogeneous magnetic field Bo, elements 12, e.g. solenoids, a power source 13 for the electromagnet, a freely displaceable examination platform 14, as well as a handle or a like control means 15 for the manual displacement of a sensor unit 20.

The operation and application of a diagnosis apparatus shown in FIG. 1 are as follows:

An examiner; a physician or the like steers by means of a manually movable examination platform 14 a patient P into the range of a homogeneous magnetic field generated by electromagnet 11. Then, by the manual control of handle 15, the examiner aims the sensor unit 20 onto a target area and simultaneously inspects the sub-sensor tissues from an ultrasonic image developed on the display means 8. After localizing in the target area a tissue portion to be characterized, the examiner switches on the NMR-analyzing system of the apparatus from the control panel 9. By means of an NMR-locking assembly 5 the NMR-analyzing system monitors the intensity of a field adjacent the sensor and transmits the information to the processing unit 10. On the display means 8 appears an image area bisecting line 21 which the examiner steers by moving the sensor unit 20 so as to pass through a tissue portion 16 to be characterized. A centering ring 19' represents an NMR-sensitive analyzing range 19 and is vertically movable along line 21 on the display means 8, said ring being also controlled by the examiner from the control panel 9. From panel 9 the examiner actuates NMR-analysis when the centering ring 19' is at the position of a tissue portion to be examined.

Figure 3:
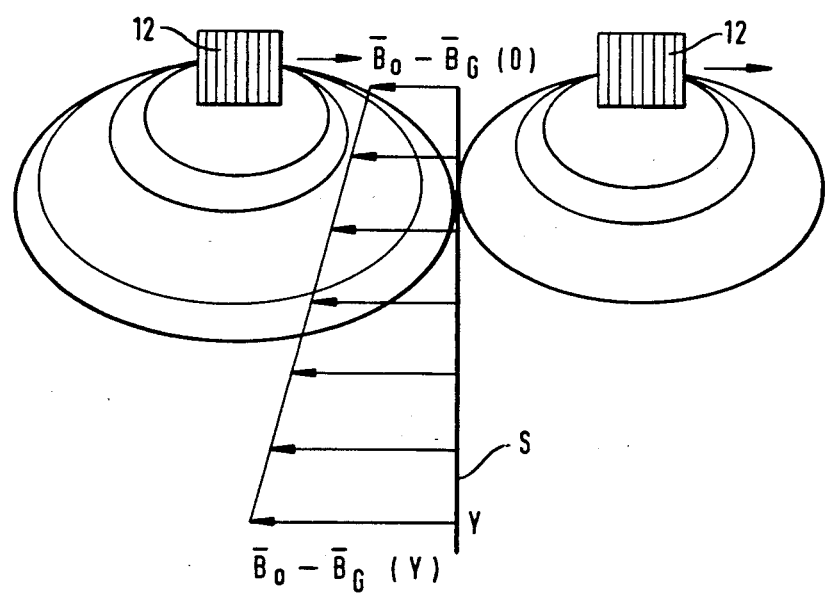
FIG. 3 shows elements intended for developing field inhomogeneites.

NMR-analysis set off in a manner that solenoids 12 activate and create a field pattern depicted in FIG. 3 which is characterized by providing on the axis of symmetry S of solenoids a field which is parallel to Bo but which has a gradient parallel to the center normal of a line connecting the solenoids. With an arrangement of FIG. 3, the field intensity increases when going further away from the line connecting the solenoids.

A processing unit 10 selects the frequency of exciting electromagnetic radiation according to the distance between a target area to be analyzed and the sensor face. The processing unit 10 emits at a selected frequency an electromagnetic pulse to the target through a coil assembly 2 serving as a transmitter/receiver; duration of the pulse is obtained from the intensity of a magnetic field generated by said coil on the target area. This can be measured experimentally and the necessary information stored in the processing unit 10. Immediately following the excitation, a current passing through solenoids 12 is switched off and the coil assembly 2 observes a precession signal of the excited nuclei, said signal being amplified in a preamplifier 3 and stored in processing unit 10. If necessary, the excitation and observation process can be repeated a sufficient number of times to reach a satisfactory signal/noise ratio. $T_1$ of the target area can be measured by applying a conventional pulse sequence with 180° pulse-delay-90° pulse. $T_2$ is obtained from the attenuation velocity of a precession signal. The results obtained are transmitted to the examiner for example as digital data. The collected NMR-information can be preferably stored by making use of the place information received from angular sensors 6. Thus, the place of origin and direction of the information collected from a patient will be clear afterwards.

The above description deals with one embodiment of an apparatus according to the invention. Other possible embodiments include combination of an ultrasonic beaming sensor into an NMR-imaging assembly e.g. by means of arrangements wherein an ultrasonic beaming assembly is by way of an oil or water bed acoustically connected to a patient's body and scanning occurs automatically and simultaneously with the NMR-image of a target. The size of an NMR-sensitive area is naturally variable depending on the equipment available. Thus, said area may represent just a small portion of the area determined by an ultrasonic beam. On the other hand, it is also possible that both areas are of the same size in which case they can, if desired, be simultaneously visualized on the display means 8. Practical difficulties in such arrangements are primarily associated with the generation of a sufficiently large homogeneous magnetic field.

The invention can with advantage be applied for diagnosing anomalies and sickly changes, e.g. due to cancer, inflammation, hemorrhage, in tissue structures of a biological object, e.g. a human body, to be examined by simultaneously collecting information on tissue structure and quality of the tissues. In practice information can be collected and stored from the tissues of healthy persons to be compared with information collected from possibly sickly tissues of body organs of patients. Another way is to collect information on different parts of a body organ of the patient himself whereby the information from the possibly sickly parts can right away be compared with the information collected from the healthy parts of said organs. It is to be understood that said reference values and information from healthy tissues can be stored in advance to include a whole database of reference information. Naturally, information on tissues which have already been diagnosed to be sick can also be stored to form a reference data base to make it easier and to speed up correct diagnosis, which is a further advantage of the invention.

I claim:

1. Diagnosis apparatus for simultaneously collecting information on tissue structure and quality of the tissues from a target, for example a human body, to be examined, said apparatus including means for transmitting ultrasonic pulses and for detecting and recording reflections from interface between the tissues, said reflections resulting from quick changes in acoustic impedance and being detected and recorded from a given target area determined by said means and selected for examination, means for processing the information obtained by said ultrasonic pulses from said target area and visually displaying the target area and the information, nuclear magnetic resonance means for collecting tissue information essentially simultaneously with the ultrasonic means from said selected area of said target under examination and establishing nuclear magnetic resonance sensitive tissue identification information from said selected area of said target area, said apparatus further including information processing means operatively connected with said nuclear magnetic resonance means for processing the tissue identification information obtained by said nuclear magnetic resonance means simultaneously with information collected by the ultrasonic means and displaying said tissue identification information along with the visual display of the information collected by said ultrasonic means, and means for effecting a magnetic field which is substantially homogeneous in said target area to be examined, said means for effecting a homogeneous magnetic field comprising an electromagnet including at least two annular magnetic elements disposed at spaced relationship with each other and about said ultrasonic transmitting means, said target to be examined being arranged to be disposed inside said magnetic elements with said target area to be examined positioned in the center area between said magnetic elements, said ultrasonic pulses transmitting and detecting means comprises an ultrasonic matrix sensor and said nuclear magnetic resonance means includes means about the sensor for effecting field gradients within the created homogeneous magnetic field and means about the sensor for transmitting radio-frequency electromagnetic pulses and for detecting nuclear magnetic resonance-signals created in said nuclear magnetic resonance-sensitive tissue identification zone by means of said pulses, a transfer unit including said ultrasonic matrix sensor and said means for transmitting radio-frequency pulses and for detecting nuclear magnetic resonance-signals being mounted to be freely transferable over said target under examination.

2. Diagnosis apparatus as claimed in claim 1, said transferable unit includes a transfer mechanism having angle sensors for registering the point of determination and establishing accurate direction of the tissue identification information collected for recording from said target under examination.

3. Diagnosis apparatus as claimed in claim 1, wherein said means for effecting field gradients comprises two magnetic source elements, disposed at a distance from each other and operable to create said homogeneous magnetic field and positioned on opposite sides of said transferable unit.

4. Diagnosis apparatus as claimed in claim 1, wherein said means for transmitting radio-frequency pulses comprises a coil assembly operable to transmit said pulses and receive the NMR-signals created in said NMR-sensitive tissue identification zone for further recording.

5. Diagnosis apparatus as claimed in claim 3, including means for displacing said NMR-sensitive tissue identification zone relative to said target area as determined by the obtained ultrasonic image.

6. Diagnosis apparatus as claimed in claim 5, wherein, for said displacement of said NMR-sensitive tissue identification zone, said coil assembly includes a signal coil means and a gradient coil means mounted to the ultrasonic probe and provided with means for changing the frequency of the created pulses to generate tissue characterization information.

7. Diagnosis apparatus as claimed in claim 1, wherein the localization and alignment of the desired NMR-sensitive tissue identification zone in a patient being arranged to be effected by means of said visualizing means, and the information collected by ultrasonic pulses as well as the tissue identification information being arranged to be visualized simultaneously.

8. Diagnosis apparatus as claimed in claim 7, wherein, for the determination of the position of said NMR-sensitive tissue identification zone in said target area to be examined, said visualizing means comprises a display means provided with an indicator the position of which is an ultrasonic image created on said display means is arranged to correspond to the position of said NMR-sensitive tissue identification zone in said target area to be examined, said display means being also used for visualizing the information collected by NMR-analysis.

9. Method for detecting and diagnosing anomalies and sickly changes, e.g. due to cancer, inflammation, hemorrhage, in tissue structures of a biological object, e.g. a human body, to be examined by simultaneously collecting information on tissue structure and quality of the tissues, said method including the steps of transmitting ultrasonic pulses into a given target area of said object selected for examination and detecting and recording the resulting reflections due to quick changes in acoustic impedance from interfaces between the tissue structures in said target area for the localization of possibly sick tissues of interest, processing the information obtained by said ultrasonic pulses from said target area for visualization thereof, simultaneously with processing the information from said ultrasonic pulses providing radio-frequency electromagnetic pulses into said localized tissue structures of interest in said target area for collecting tissue identification information provided by nuclear magnetic resonance or NMR-phenomenon from said object to be examined, and simultaneously processing the tissue identification information obtained by NMR-analysis with the information collected by the ultrasonic pulses to produce information related to the character of the tissue.

10. A method as claimed in claim 9, including the step of visualizing the information collected by NMR-analysis simultaneously with the ultrasonic image of the target area.

11. A method as claimed in claim 9 or 10, including the steps of storing NMR-information of a number of separate healthy biological tissues and comparing the NMR-information received from the tissues in the target area of the object under examination with said stored NMR-information of healthy tissues respectively.

* * * * *